United States Patent [19]

Sawamura

[11] Patent Number: 5,101,101

[45] Date of Patent: Mar. 31, 1992

[54] METHOD OF DETECTING OPAQUE FOREIGN ARTICLE FROM AMONG TRANSPARENT BODIES UTILIZING POLARIZED LIGHT

[75] Inventor: Masaki Sawamura, Tokyo, Japan

[73] Assignee: Toyo Glass Co., Ltd., Tokyo, Japan

[21] Appl. No.: 565,530

[22] Filed: Aug. 10, 1990

[30] Foreign Application Priority Data

Aug. 17, 1989 [JP] Japan .................................. 1-210573

[51] Int. Cl.$^5$ ............................................. G01N 9/04
[52] U.S. Cl. .................................. 250/223 R; 250/225
[58] Field of Search ................... 250/225, 223 R, 572, 250/571, 574, 575, 226; 356/445, 446, 447, 448, 369, 435, 380; 209/577, 587, 636

[56] References Cited

U.S. PATENT DOCUMENTS

3,197,647 7/1965 Fraenkel ............................. 250/225
4,730,932 3/1988 Iga et al. ............................. 356/432

Primary Examiner—David C. Nelms
Assistant Examiner—T. Davenport
Attorney, Agent, or Firm—Sughrue, Mion, Zinn, Macpeak & Seas

[57] ABSTRACT

A method of detecting an opaque foreign article from among transparent bodies which assures a distinct difference between detection signals originating from a transparent body and an opaque foreign article and a high S/N ratio in such detection signals and is improved in accuracy in detecting operation. The method comprises the steps of scanning, while an object for the detection which may be one of transparent bodies or an opaque foreign article existing in such transparent bodies is being moved, the object for the detection by a beam of linearly polarized light, and detecting reflected light from the object for the detection upon each scanning using an optical sensor such as a charge coupled device camera by way of a polarizing filter.

7 Claims, 6 Drawing Sheets

METHOD OF DETECTING OPAQUE FOREIGN ARTICLE FROM AMONG TRANSPARENT BODIES UTILIZING POLARIZED LIGHT

BACKGROUND OF THE INVENTION

1. Field of the Invention

This invention relates to a method of detecting an opaque foreign article such as a stone or a pottery piece from among transparent bodies such as, for example, glass pieces of recovered cullets or the like.

2. Description of the Prior Art

A method of detecting an opaque foreign article from among transparent bodies is already known and is disclosed, for example, in U.S. Pat. No. 4,730,932. According to the known method, a laser beam is irradiated into a spot upon an object for the inspection which is being transported on a conveyor line, and irregular reflection components of reflected light from the object are detected and converted into electric signals by means of a photoelectric transducer. Then, output levels of such electric signals are checked in order to determine whether the object for the inspection is either a glass piece or an opaque foreign article.

With the detecting method which is based merely on such irregular reflection components of reflected light, however, output levels of electric signals originating from a glass piece and an opaque foreign article do not exhibit a distinct difference, and the S/N ratio (signal-to-noise ratio) of such electric signals is low. Consequently, satisfactory results of detection cannot be obtained.

SUMMARY OF THE INVENTION

It is an object of the present invention to provide a method of detecting an opaque foreign article from among transparent bodies which assures a distinct difference between detection signals originating from a transparent body and an opaque foreign article and a high S/N ratio in such detection signals and is improved in accuracy in detecting operation.

In order to attain the object, according to an aspect of the present invention, there is provided a method of detecting an opaque foreign article from among transparent bodies, which comprises the steps of scanning, while an object for the detection which may be one of transparent bodies or an opaque foreign article existing in such transparent bodies is being moved, the object for the detection by a beam of linearly polarized light, and detecting reflected light from the object for the detection upon each scanning using an optical sensor such as a charge coupled device camera by way of a polarizing filter.

With the detecting method, most of a beam of linearly polarized light which is irradiated upon a transparent body passes through the transparent body. Even if part of the linearly polarized light beam is reflected by the transparent body, it is subsequently cut by the polarizing filter because almost all of it is a linearly polarized light component, and only when there is some irregular condition on a reflecting face of the transparent body, a very small amount of a circularly polarized light component can pass through the polarizing filter. Accordingly, only a very small amount of reflected light will be introduced into the optical sensor. On the other hand, most of a linearly polarized light beam which is irradiated upon an opaque foreign article is scattered by a surface of the opaque foreign article while part of the linearly polarized light beam is absorbed by the surface of the opaque foreign article. Most of such scattered reflected light is circularly polarized light and almost always passes through the polarizing filter. Consequently, such scattered reflected light is introduced by a great amount into the optical sensor.

Thus, since an object for the detection is scanned by a linearly polarized light beam and reflected light is detected by the optical sensor by way of the polarizing filter, the difference between inputs to the optical sensor of reflected light from a transparent body and an opaque foreign article appears distinctly. Consequently, a transparent body and an opaque foreign article can be detected and separated precisely with a simple optical construction.

According to another aspect of the present invention, there is provided a method of detecting an opaque foreign article from among transparent bodies, which comprises the steps of scanning, while an object for the detection which may be one of transparent bodies or an opaque foreign article existing in such transparent bodes is being moved, the object for the detection by a plurality of times by a beam of light, detecting reflected light from the object for the detection upon each scanning using an optical sensor such as a charge coupled device camera, binary digitizing outputs of the optical sensor, and ANDing the binary digitized outputs for a plurality of scanning operations.

With the detecting method, an object for the detection which may be either a transparent body or an opaque foreign article is scanned at different locations thereof by a plurality of times by a light beam, and reflected light from the object for the detection is detected for each scanning by the optical sensor and then digitized. The amount of reflected light to be introduced into the optical sensor is small where the object for the detection is a transparent body but is large where the object is an opaque foreign article, and besides the changing rate of reflected light is high where the object is a transparent body but is low where the object is an opaque foreign article. Accordingly, when binary digitized outputs of the optical sensor are ANDed for a plurality of times of scanning operations, the value obtained is smaller than any of the binary digitized outputs where they originate from a transparent body, but it is higher than any of the binary digitized outputs where they originate from an opaque foreign article. Consequently, the difference between the two values is greater and more distinct than the difference between optical inputs to the optical sensor.

Since an object for the detection which may be a transparent body or an opaque foreign article is scanned by a plurality of times and digital signals obtained by such scanning operations by a plurality of times are ANDed in this manner, a transparent body and an opaque foreign article can be detected and separated more precisely than ever, and besides the S/N ratio is improved.

According to a further aspect of the present invention, there is provided a method of detecting an opaque foreign article from among transparent bodies, which comprises the steps of scanning, while an object for the detection which may be one of transparent bodies or an opaque foreign article existing in such transparent bodies is being moved, the object for the detection by a plurality of times by a beam of linearly polarized light, detecting reflected light from the object for the detection upon each scanning using an optical sensor such as a charge coupled device camera by way of a polarizing filter, binary digitizing outputs of the optical sensor, and ANDing the binary digitized outputs for a plurality of scanning operations.

With the detecting method, similar operations and effects to those of the detecting methods according to the first and second aspects of the present invention can be anticipated.

The above and other objects, features and advantages of the present invention will become apparent from the following description and the appended claims, taken in conjunction with the accompanying drawings.

DETAILED DESCRIPTION OF THE PREFERRED EMBODIMENT

Figure 1:
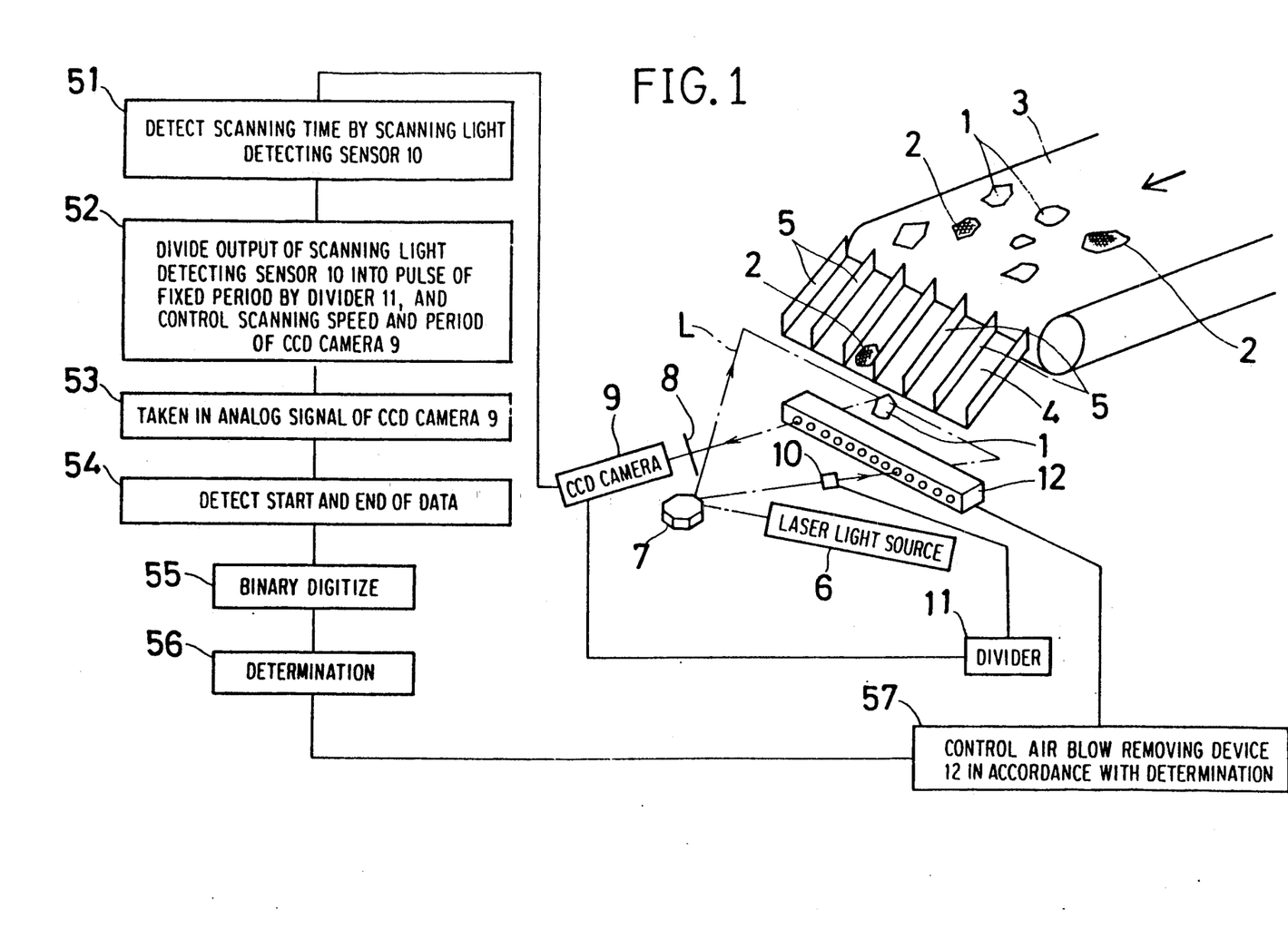
FIG. 1 is a generalized flow diagram illustrating a detecting method according to the present invention.

Referring first to FIG. 1, there is illustrated a detecting method according to the present invention. A large number of objects for the detection are transported on a belt conveyor or a vibrating feeder 3 to a drop chute 4. Such objects for the detection are transparent bodies such as, for example, pieces 1 of glass in which stones, pottery pieces and so forth may be mixed as opaque foreign articles 2, and here, the detecting method of the present invention is applied to detect such opaque foreign particles 2 from among glass pieces 1. At the drop chute 4, the objects for the detecting are dropped in a separated condition in several rows by a plurality of separating fins 5 of the drop chute 4. While the objects for the detection including glass pieces 1 and opaque foreign substances 2 are dropping, they are scanned a plurality of times by a linearly polarized laser beam L along a transverse line in a direction perpendicular to the dropping direction at a predetermined height.

In particular, a laser beam emitted from a laser light source 6 is reflected by a polygon scanner 7 which is constantly rotating at a fixed speed in a predetermined direction so as to make a scanning operation as a linearly polarized laser beam L. The period of such scanning operation is determined such that a same object for the detection can be scanned two or more times while it drops. Accordingly, the object for the detection will be scanned not at a same location thereof two or three times but at two or more different locations thereof.

Reflected light from an object for the detection is introduced into a CCD (charge coupled device) camera 9 by way of a polarizing filter 8 and is detected as an electric signal by the CCD camera 9. In order to synchronize such detecting operation with a scanning operation by a linearly polarized laser beam L, scanning light is detected by a scanning light detecting sensor 10 (step 51) located within a scanning range of scanning light from the polygon scanner 7, and a detection signal of the scanning light detecting sensor 10 is divided into a pulse signal by a divider 11 and then fed back to the CCD camera 9 in order to control a scanning speed and period of the CCD camera 9 (step 52), for example, by way of a suitable control circuit (not shown). While such control is being executed, an analog signal of the CCD camera 9 is taken in (step 53) by the control circuit, and the start and the end of the data of the analog signal are detected as a preprocessing step (step 54) also by the control circuit. Then, the analog signal is binary digitized (step 55) by a binary digitizer not shown, and the binary data obtained is checked by a determination circuit (not shown) to determine whether the object for the detection is either a glass piece 1 or an opaque foreign article 2 as hereinafter described (step 56). Then, in case the result of the determination represents an opaque foreign article 2, an air blow removing device 12 is controlled by a controlling circuit (not shown) therefor in response to a removing signal from the determination circuit so that the opaque foreign article 2 may be separated from glass pieces 1 by an air blow produced by the air blow removing device 12 while it is dropping (step 57).

It is to be noted that, while such operations as described above are executed by several electric circuits such as the control circuit, binary digitizing circuit, determination circuit and controlling circuit, they may otherwise be executed suitably by a microcomputer or like electronic means which operates in accordance with a flow of operations including such steps 51 (or 52) to 57 illustrated in FIG. 1. It is also to be noted that, since the scanning light detecting sensor 10 detects scanning light at a fixed position within the scanning range of scanning light (step 51), a period of a scanning operation can be detected from two successive timings of detection of scanning light by the scanning light detecting sensor 10.

Figure 2:
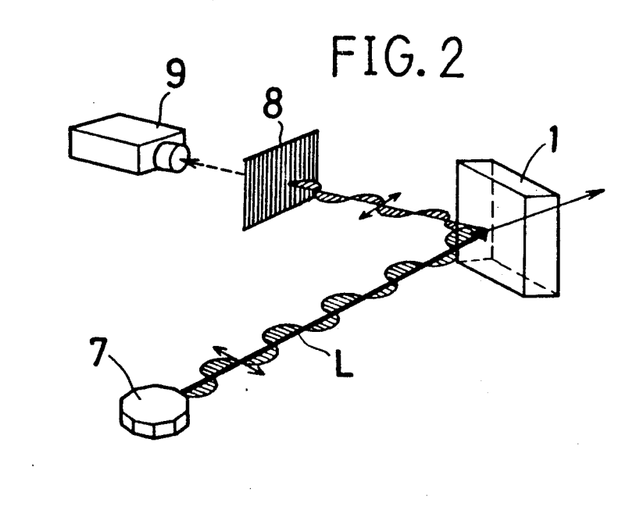
FIGS. 2 and 3 are schematic illustrations showing reflection and transmission of light by and through a glass piece.
Figure 3:
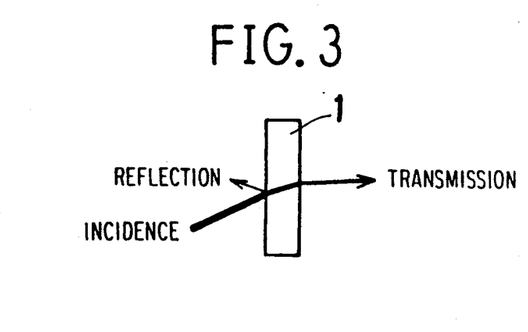

Thus, according to the present embodiment, a linearly polarized laser beam L is irradiated upon glass pieces 1 and opaque foreign articles 2 which are dropping, and reflected light from them is detected by the CCD camera 9 by way of the polarizing filter 8. When the linearly polarized laser beam L is irradiated upon a glass piece 1, most of the beam L passes through the glass piece 1 while only a small fraction of it is reflected by the glass piece 1, as shown in FIGS. 2 and 3. Here, in case the reflecting face of the glass piece 1 is flat and accordingly reflects light regularly, the light after it is reflected by the reflecting face of the glass piece 1 remains as linearly polarized light. Consequently, the reflected light will be cut by the polarizing filter 8 and will not be introduced into the CCD camera 9. On the other hand, in case the reflecting face of the glass piece 1 is uneven or has some scratches or the like thereon, or in case light is reflected from the opposite ends of the glass piece 1, the reflected light will be circularly polarized light, and only one component of the reflected light will pass through the polarizing filter 8. However, this component is very small in amount.

Figure 4:
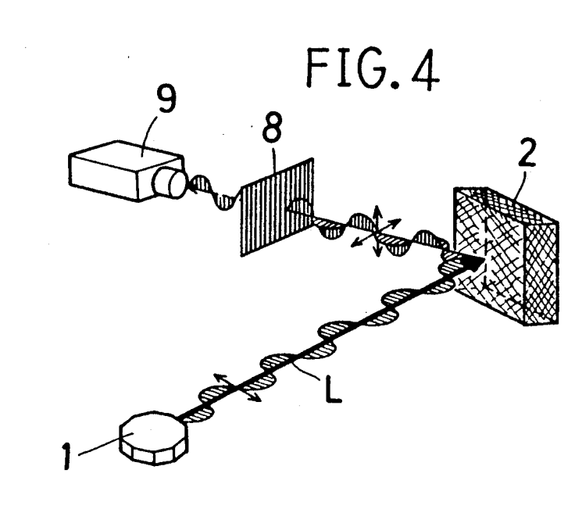
FIGS. 4 and 5 are schematic illustrations showing reflection of light by an opaque foreign substance.
Figure 5:
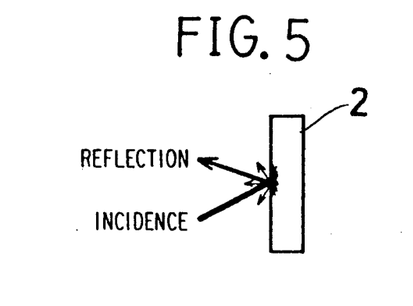

Meanwhile, when the object for the detection is an opaque foreign article 2, most of a linearly polarized laser beam L is scattered but irregularly by a surface of the opaque foreign article 2 while part of the linearly polarized laser beam L is absorbed, as shown in FIGS. 4 and 5. Since such irregularly scattered light is circularly polarized light, most of the light passes through the polarizing filter 8 and is introduced into the CCD camera 9. The amount of light then is very large in comparison with that when the object for the detection is a glass piece 1.

Accordingly, the output of the CCD camera 9 which may be an output of a CCD line sensor presents a great difference depending upon whether the object for the detection is a glass piece 1 or an opaque foreign article 2.

Figure 6A:
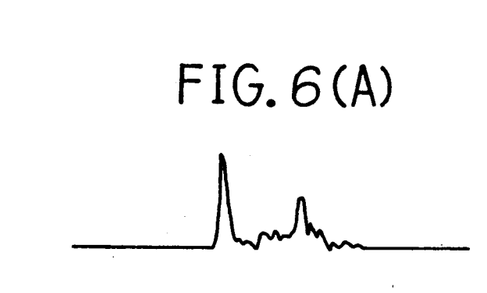
FIGS. 6(A) and 6(B) are waveform diagrams showing outputs of a CCD (charge coupled device) camera when it receives reflected light from a glass piece without and with a polarizing filter interposed in the passage of the reflected light, respectively.
Figure 6B:
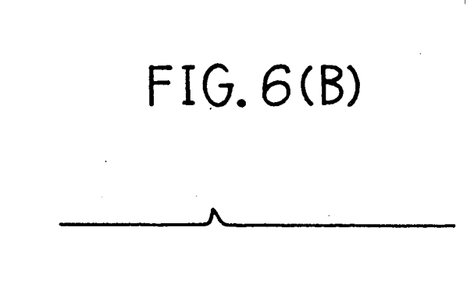
Figure 7A:
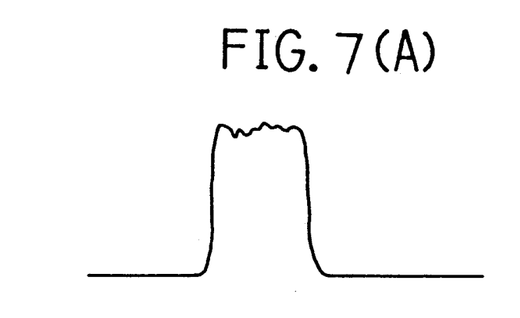
FIGS. 7(A) and 7(B) are waveform diagrams showing outputs of the CCD camera when it receives reflected light from an opaque foreign article without and with the polarizing filter interposed in the passage of the reflected light, respectively.
Figure 7B:
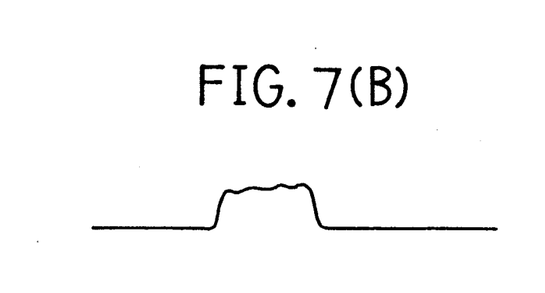

FIGS. 6(A) and 6(B) show output waveforms when the CCD line sensor measures reflected light from a glass piece 1. In particular, FIG. 6(A) shows such an output waveform when the polarizing filter 8 is not used, and FIG. 6(B) shows such output waveform when the polarizing filter 8 is used. FIGS. 7(A) and 7(B) show similar output waveforms when the CCD line sensor measures reflected light from an opaque foreign substance 2 without and with the polarizing filter 8 interposed in the passage of the reflected light, respectively.

As can be seen from those figures, in case the polarizing filter 8 is not used, when the CCD camera 9 receives reflected light from a glass piece 1, it produces an output of a sawtooth waveform which exhibits large and irregular variations and is high in level, but when the CCD camera 9 receives reflected light from an opaque foreign article 2, it produces an output having a waveform resembling a rectangular waveform which exhibits small variations and is high in level and continuous in time. Although the two outputs are different in waveform, they do not have a great difference in level or in duration. On the other hand, in the case where the polarizing filter 8 is used, an output of the CCD camera 9, when it receives reflected light from a glass piece 1, makes a single sharp and short pulse which is low in level. When the CCD camera 9 receives reflected light from an opaque foreign article 2, camera 9 produces an output in the form of a regular rectangular wave which is much higher in level than that of the former case, and is sufficiently long in duration.

While signals obtained upon optical scanning of a glass piece 1 and an opaque foreign article 2 exhibit distinct differences due to optical processing before light is introduced into the CCD camera 9, such differences are made more precise in electric signal processing by the following method.

Figure 8:
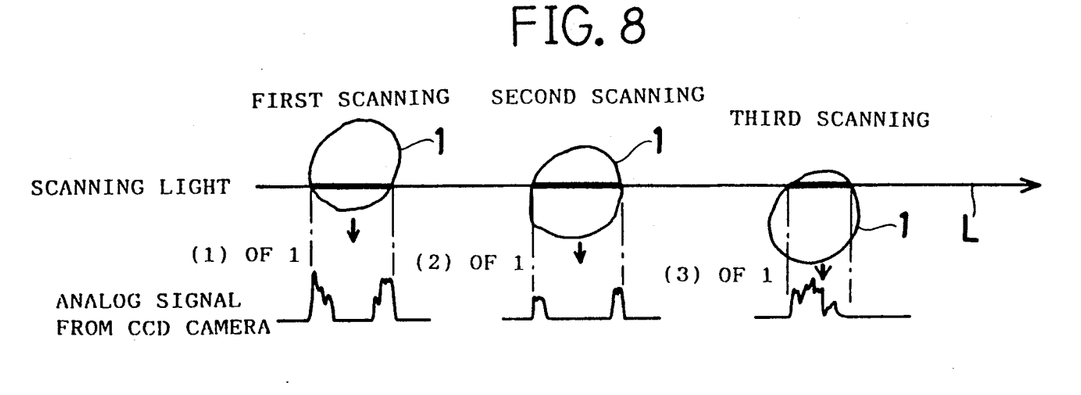
FIG. 8 is a diagram illustratively showing a scanning manner for a glass piece and a waveform of an analog signal of the CCD camera upon such scanning.
Figures 11, 12, 13:
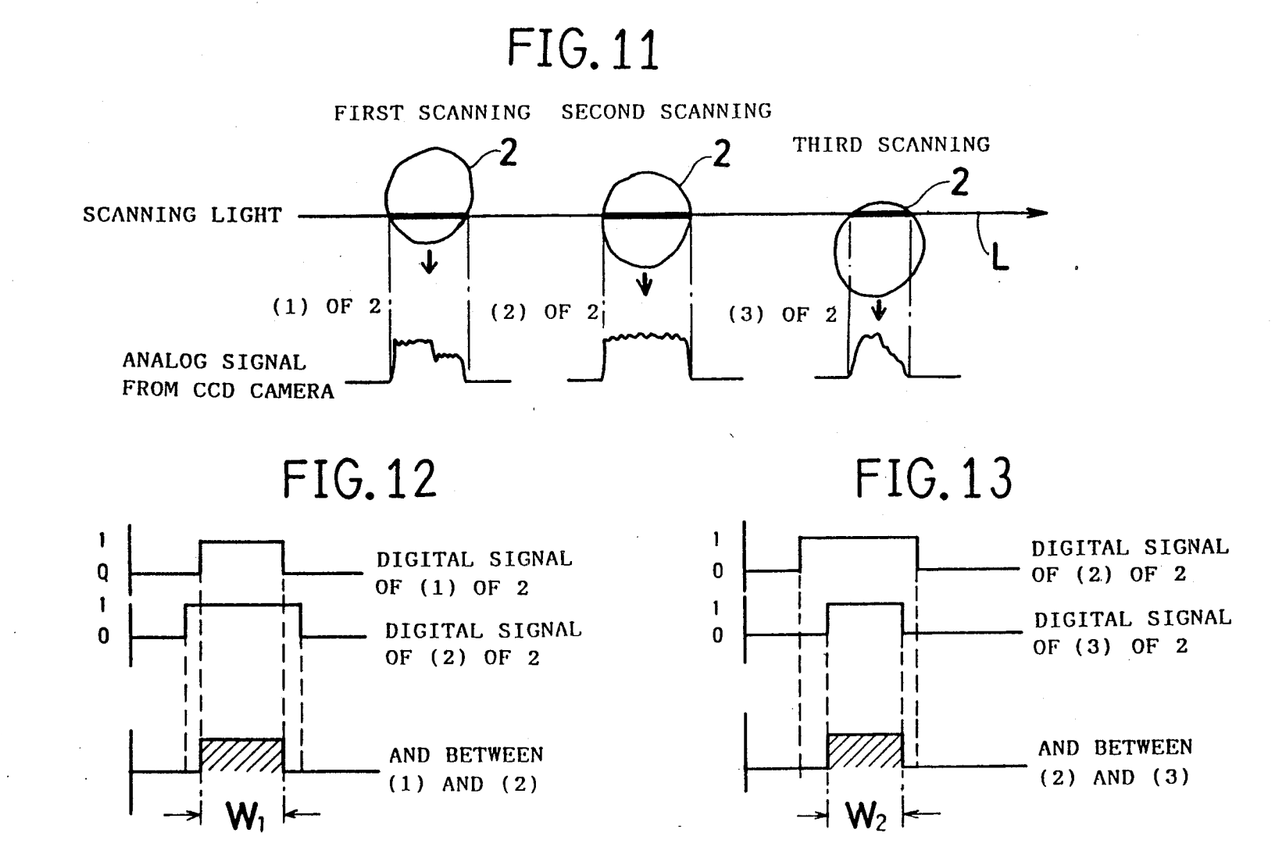
FIG. 11 is a diagram illustratively showing a scanning manner for an opaque foreign article and a waveform of an analog signal of the CCD camera upon such scanning.
FIGS. 12 and 13 are time charts illustrating digital processing of signals originating from an opaque foreign article.

It is assumed here that a glass piece 1 is scanned three times by a linearly polarized laser beam L while the piece 1 is dropping as, shown in FIG. 8 (a scanned location of the glass piece 1 is displaced as the glass piece 1 drops). Analog signals from the CCD camera 9 upon first, second and third scanning operations, which are taken in at step 53 of FIG. 1 are such as shown at (1) of 1, (2) of 1 and (3) of 1 of FIG. 8, respectively. It is also assumed that an opaque foreign substance 2 is scanned three times similarly by a linearly polarized laser beam L while it is dropping as shown in FIG. 11, and analog signals from the CCD camera 9 upon first, second and third scanning operations are such as shown at (1) of 2, (2) of 2 and (3) of 2 of FIG. 11, respectively.

Figure 9:
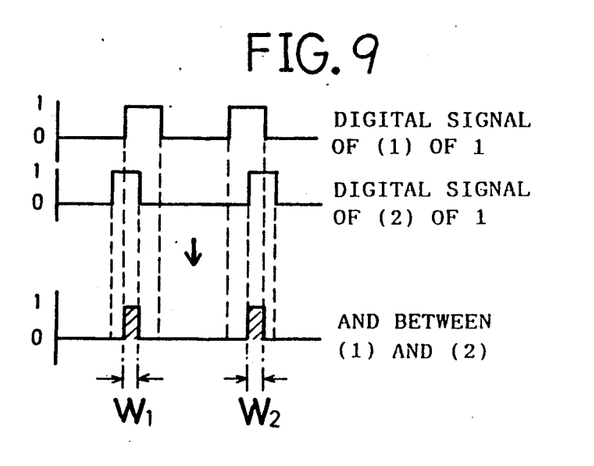
FIGS. 9 and 10 are time charts illustrating digital processing of signals originating from a glass piece.
Figure 14:
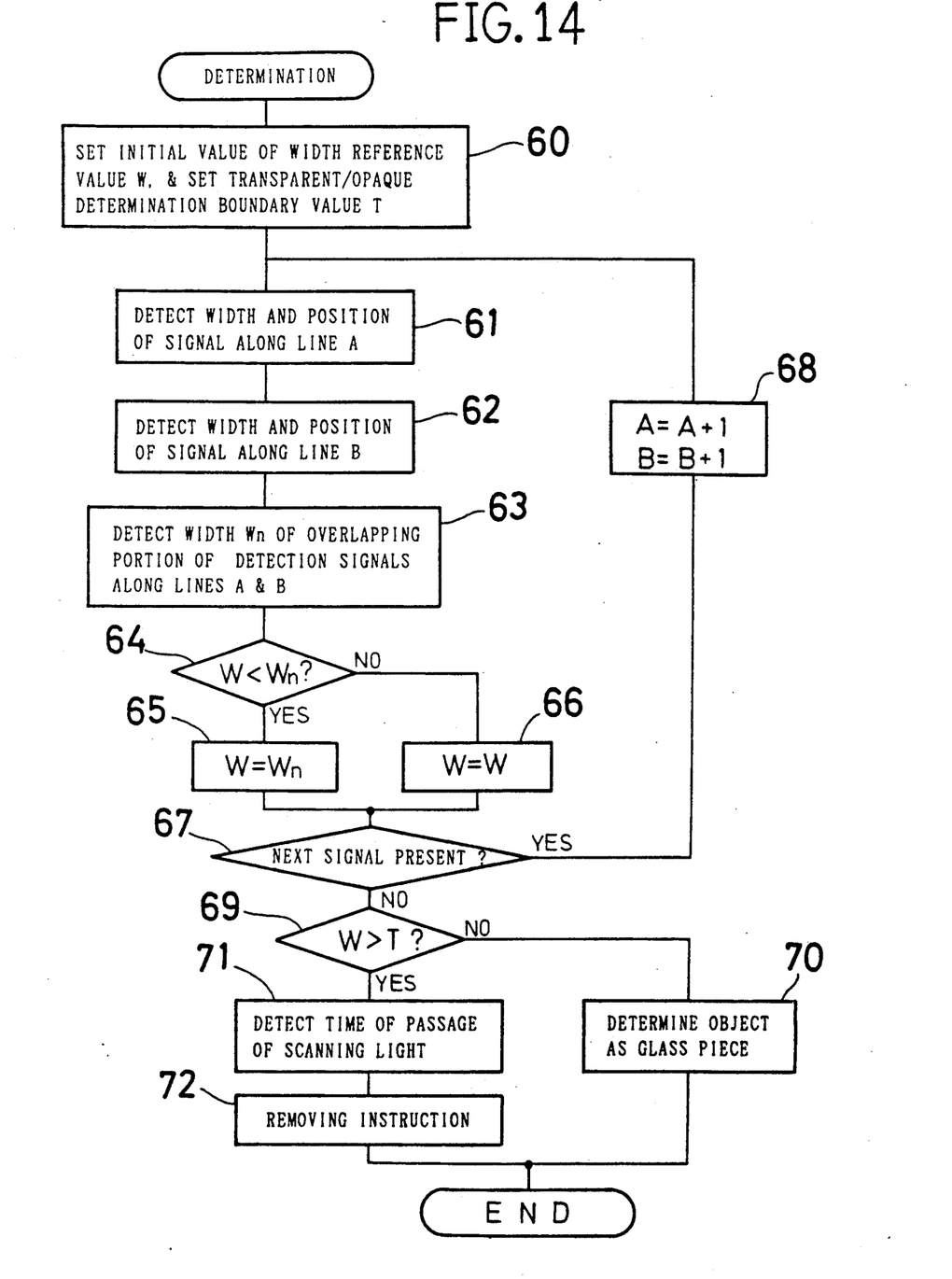
FIG. 14 is a flow chart illustrating determination processing.

Referring to FIG. 14, after those analog signals are binary digitized into digital signals at step 55 of the flow chart of FIG. 1, a width reference value W is set to a predetermined initial value and a transparent/opaque determination boundary value T is set first at step 60. Subsequently at step 61, a width and a position of a signal along a scanning line A (initially in the first scanning operation) are detected, and then at step 62, a width and a position of another signal along a next scanning line B (initially in the second scanning operation) are detected similarly, whereafter the signals from the lines A and B are ANDed (ANDed) at step 63. Here, in other words, a width $W_n$ ($W_1$, $W_2$, ...) of an overlapping portion of the signals from the line A and the next line B is detected. FIG. 9 is a time chart illustrating operations at steps 61 to 63 when a glass piece 1 is scanned as illustrated in FIG. 8, and FIG. 12 is a time chart illustrating similar operations when an opaque foreign substance 2 is scanned as illustrated in FIG. 11.

Subsequently at step 64, it is judged whether or not the detected width $W_n$ is greater than the width reference value W ($W_n > W$), and in case the former is greater than the latter, $W_n$ is stored as the width reference value W, that is, the detected width $W_n$ is set as a new width reference value W, at step 65. On the contrary when $W_n$ is not greater than W, the detected width $W_n$ is not adopted, but W is maintained or stored as it is at step 66.

The sequence advances from step 65 or 66 to step 67 at which it is judged whether or not there is a digital signal from a next scanning line, and in case there is a digital signal, the scanning lines A and B are advanced, at step 68, by one line to A+1 and B+1, respectively, and a width $W_n$ of an overlapping portion is detected similarly as described above (refer to FIGS. 10 and 13). Then, the processing from step 61 to step 65 or 66 is repeated until it is judged at step 67 that there is no digital signal any more. Since the value of $W_n$ is updated as new W only at step 65 when $W_n$ is greater than W at step 64, the processing from step 61 to step 65 or 66 is after all processing to extract a maximum detected value $W_n$ among detected values from the first to last lines, and when it is judged at step 67 that there is no digital signal input any more, W exhibits such maximum detected value.

Figure 10:
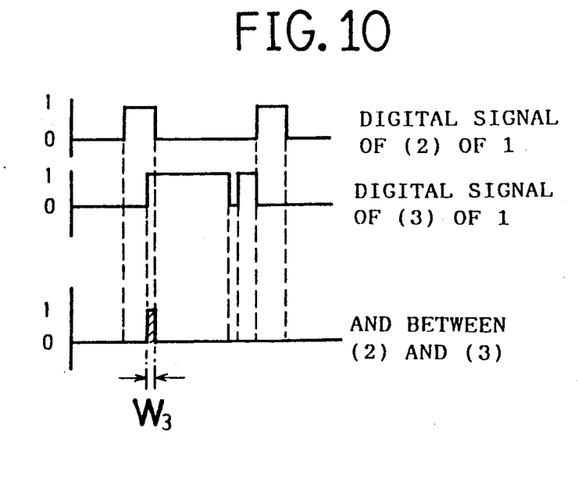

Accordingly, as can be seen from FIGS. 9 and 10, the width of a digital signal originating from a glass piece 1 is small originally, and besides where the object for the detection is a glass piece 1, even if regularly reflected light is detected which exhibits an uneven waveform due to such local reflection as described above, since a location scanned by a laser beam is displaced for each scanning operation, the possibility that a similar regularly reflected condition may take place twice successively is very low and digital signals obtained by twice scanning operations are displaced in position in the scanning direction. Consequently, a detected width $W_n$ obtained by ANDing the thus displaced two digital signals is smaller than the width of any one of the digital signals.

On the other hand, the width of a digital signal originating from an opaque foreign article 2 is small originally as shown in FIGS. 12 and 13, and besides where the object for the detection is an opaque foreign substance 2, reflected light of a high level is detected successively, and consequently, positions of digital signals obtained by twice scanning operations will be overlapped with each other. Consequently, a detected width $W_n$ obtained by ANDing the two digital signals is very great comparing with that obtained from signals originating from a glass piece 1. Besides, since only a maximum width value among them is adopted, the difference is increased further.

At subsequent step 69, it is judged whether or not the maximum detected value W is higher than the transparent/opaque determination boundary value T (W>T), and in case the former is not higher than the latter, it is determined at step 70 that the object for the detection is a glass piece 1. In this case, the air blow removing device 12 is not rendered operative. On the contrary, in case the maximum detected value W is higher than the transparent/opaque determination boundary value T at step 69, a point of time at which scanning light passes the scanning light detecting sensor 10 is detected based on detection by the scanning light detecting sensor 10 at step 71, and at a point of time when the opaque foreign article 2 drops to a height at which it cannot be scanned by the laser beam L any more, a removing instruction is developed at step 72 to render the air blow removing device 12 operative. In this instance, the air blow removing device 12 produces, by control at step 57 of FIG. 1, an air blow only at a position corresponding to the dropping opaque foreign article 2 to blow off and remove the opaque foreign article 2.

It is to be noted that such removal and scanning by a laser beam may otherwise be performed at any location other than the dropping location or may be performed by any other means than by an air blow. Further, it may be applicable to scan with a beam of light other than a laser beam, to AND digital signals obtained by three or more scanning operations or to detect reflected light by means of an optical sensor other than a CCD line sensor.

Having now fully described the invention, it will be apparent to one of ordinary skill in the art that many changes and modifications can be made thereto without departing from the spirit and scope of the invention as set forth herein.

What is claimed is:

1. A method of detecting an opaque foreign article from among transparent bodies, comprising the steps of scanning, while an object for the detection which may be one of transparent bodies or an opaque foreign article existing among such transparent bodies is being moved, the object for the detection by a beam of linearly polarized light, and detecting reflected light from the object for the detection upon each scanning using an optical sensor.

2. A method of detecting an opaque foreign article from among transparent bodies, comprising the steps of scanning, while an object for the detection which may be one of transparent bodies or an opaque foreign article existing in such transparent bodes is being moved, the object for the detection by a plurality of times by a beam of light, detecting reflected light from the object for the detection upon each scanning using an optical sensor, binary digitizing outputs of said optical sensor, and ANDing the binary digitized outputs for a plurality of scanning operations.

3. A method of detecting an opaque foreign article from among transparent bodies, comprising the steps of scanning, while an object for the detection which may be one of transparent bodies or an opaque foreign article existing in such transparent bodes is being moved, the object for the detection by a plurality of times by a beam of linearly polarized light, detecting reflected light from the object for the detection upon each scanning using an optical sensor by way of a polarizing filter, binary digitizing outputs of said optical sensor, and ANDing the binary digitized outputs for a plurality of scanning operations.

4. The method of detecting an opaque foreign article recited in claim 1, wherein said optical sensor is a charge coupled device camera receiving reflected light by way of a polarizing filter.

5. The method of detecting an opaque foreign article recited in claim 2, wherein said optical sensor is a charge coupled device camera.

6. The method of detecting an opaque foreign article recited in claim 3, wherein said optical sensor is a charge coupled device camera.

7. The method of detecting an opaque foreign article recited in claim 4, wherein said scanning is performed a plurality of times on each object for detection, and said linearly polarized light is applied to each object for detection in a different spot on said object for each scan.

* * * * *